(12) United States Patent
Barsoum

(10) Patent No.: US 8,864,838 B2
(45) Date of Patent: Oct. 21, 2014

(54) ACETABULAR CUP BUTTRESS

(75) Inventor: Wael K. Barsoum, Bay Village, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 787 days.

(21) Appl. No.: 12/403,394

(22) Filed: Mar. 13, 2009

(65) Prior Publication Data

US 2009/0234460 A1 Sep. 17, 2009

Related U.S. Application Data

(60) Provisional application No. 61/036,487, filed on Mar. 14, 2008.

(51) Int. Cl.
*A61F 2/34* (2006.01)
*A61F 2/30* (2006.01)

(52) U.S. Cl.
CPC .............. *A61F 2/34* (2013.01); *A61F 2002/305* (2013.01); *A61F 2002/3401* (2013.01); *A61F 2002/30729* (2013.01); *A61F 2002/30578* (2013.01); *A61F 2/30728* (2013.01); *A61F 2002/30383* (2013.01); *A61F 2220/0025* (2013.01); *A61F 2002/342* (2013.01)
USPC ...................................... 623/22.36; 623/22.38

(58) Field of Classification Search
CPC .............. A61F 2/34; A61F 2220/0025; A61F 2220/0033; A61F 2220/0044
USPC ............. 623/22.11–22.19, 22.2–22.39, 22.42
See application file for complete search history.

(56) References Cited

U.S. PATENT DOCUMENTS

| 5,425,778 | A | * | 6/1995 | Zichner et al. ............. 623/22.29 |
| 5,871,548 | A | * | 2/1999 | Sanders et al. ............. 623/22.36 |
| 6,908,486 | B2 | * | 6/2005 | Lewallen .................... 623/22.21 |

* cited by examiner

*Primary Examiner* — Tom Sweet
*Assistant Examiner* — Christopher D Prone
(74) *Attorney, Agent, or Firm* — Tarolli, Sundheim, Covell & Tummino LLP

(57) ABSTRACT

A buttress plate for retaining an acetabular cup implanted in an acetabulum is provided. The buttress plate includes a base having a first end and a second end. The first end extends along a plane and includes at least one passage for receiving a fastener to secure the base to the acetabulum. The second end includes a lip extending transverse to the plane for securing the acetabular cup within the acetabulum.

8 Claims, 5 Drawing Sheets

US 8,864,838 B2

ACETABULAR CUP BUTTRESS

RELATED APPLICATION

This application claims priority from U.S. Provisional Patent Application Ser. No. 61/036,487, filed on Mar. 14, 2008, the subject matter of which is incorporated herein by reference.

TECHNICAL FIELD

The present invention is directed to bone fixation and, in particular, is directed to a method and apparatus for buttressing a prosthetic acetabular component for a deficient acetabulum.

BACKGROUND OF THE INVENTION

Every year, thousands of individuals undergo total hip replacement (THR) as a result of degeneration or otherwise excessive damage to the acetabulum. This damage causes irregular and/or painful articulation between the femoral head and the acetabulum during normal movement of the leg and hip. It therefore becomes necessary to replace the damaged articulation site with a prosthetic implant that can adequately manage the normal forces encountered at the site while maintaining a sufficient range of motion between the femur and pelvic girdle.

A THR procedure typically involves resecting a portion or all of the acetabulum so that a prosthetic component mimicking the acetabulum can be installed in its place. The cup is contoured and constructed such that its functionality closely resembles that of the native acetabulum. The femoral head may also be partially or fully resected to accommodate a prosthetic stem and head that will articulate with the prosthetic cup.

The efficacy of current acetabular cups lies in the ability to retain a secure connection between the cup and the pelvic girdle. By maintaining a strong connection, the ability of the surrounding bone to heal is improved, as is the reliability of the replaced articulation site. However, due to constant and variable articulation between the femoral head and the acetabular cup, the cup may loosen over time. This movement may contribute to a weakened articulation site or may make the femoral head susceptible to slippage out of the cup, resulting in severe pain and discomfort. Another contributing factor to the performance decline of an acetabular cup can be the complex anatomical geometry of the pelvic girdle. This geometry may make it difficult to ensure a lasting, rigid connection between the cup and the bone. Current cups use bone cement, friction, and/or fasteners/screws to directly secure the cup to the pelvic girdle. For the above reasons, these fastening constructions can fail to ensure proper fixation of the cup within the acetabulum.

Accordingly, there is a need for an apparatus and method for ensuring that prosthetic acetabular cups are securely fitted to the pelvic girdle to ensure proper healing and reliable articulation with the femoral head.

SUMMARY OF THE INVENTION

In accordance with the present invention, a buttress plate for retaining an acetabular cup implanted in an acetabulum is provided. The buttress plate includes a base having a first side portion and a second side portion. The first side portion extends along a plane and includes at least one passage for receiving a fastener to secure the base to the acetabulum. The second side portion includes a lip extending transverse to the plane for securing the acetabular cup within the acetabulum.

In accordance with another embodiment of the present invention, a method is provided for retaining an acetabular cup implanted in an acetabulum. The acetabular cup is placed within the acetabulum, wherein the cup is pre-contoured to the acetabulum. A buttress plate is fastened to a lateral surface of the acetabulum, the plate including a base having a first side portion and a second side portion, the first side portion extending along a plane and including at least one passage for receiving a fastener to secure the base to the acetabulum, the second side portion including a lip extending transverse to the plane for securing the acetabular cup within the acetabulum.

In accordance with another embodiment of the present invention, a buttress plate for retaining an acetabular cup implanted in an acetabulum is provided. A buttress plate includes an arcuate base having a first side portion and a second side portion. The first side portion extends along a plane and includes at least one tab extending outward from the first side portion. Each of the at least one tabs includes at least one passage for receiving a fastener to secure the base to the acetabulum. The second side portion includes an arcuate lip extending transverse to the plane for securing the acetabular cup within the acetabulum. The base further includes means for engaging bone and means for promoting bone growth

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION

Figure 1:
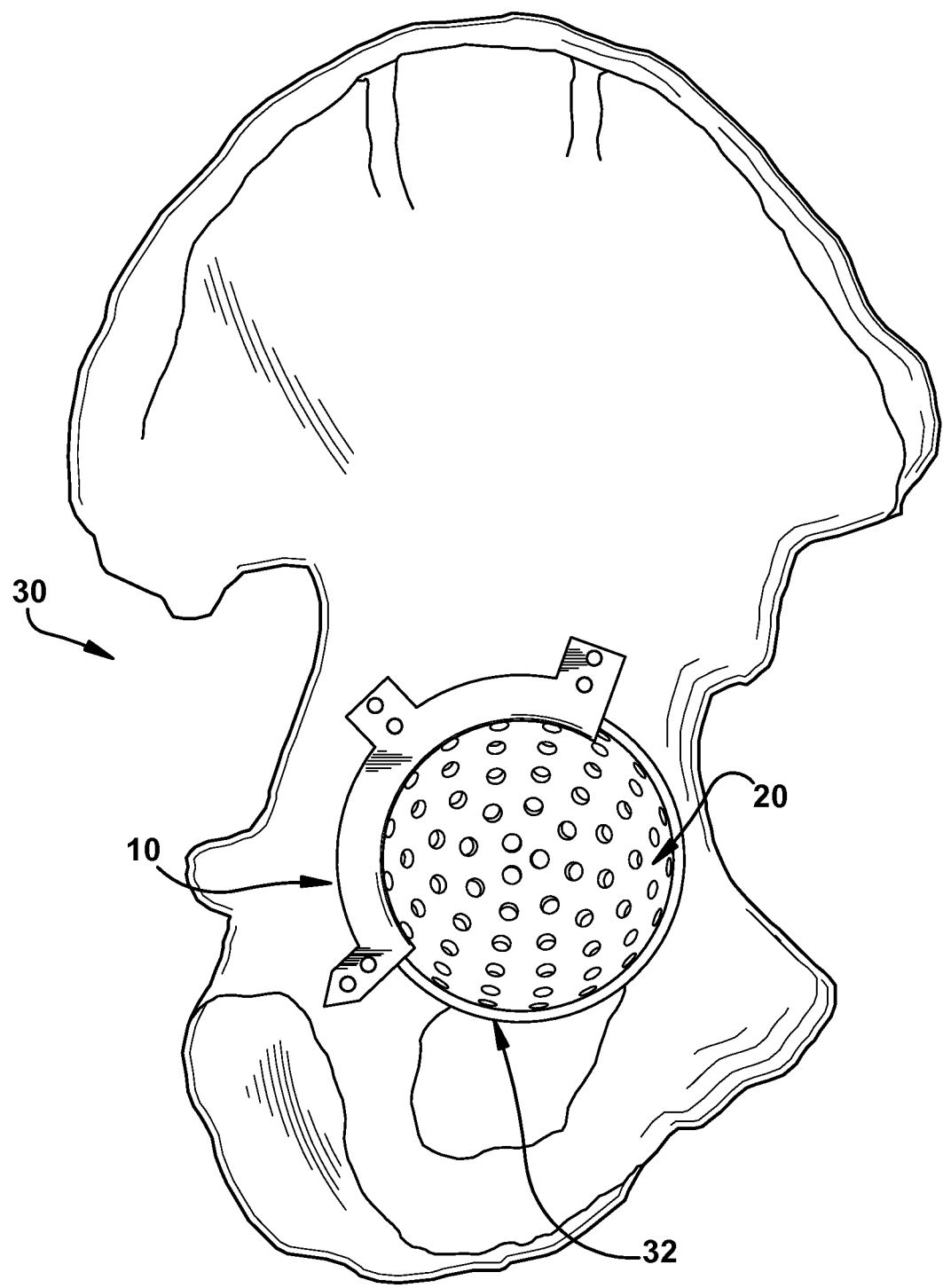
FIG. 1 is a schematic illustration of an acetabular buttress plate in accordance with an embodiment of the present invention.

The present invention is directed to bone fixation and, in particular, is directed to a method and apparatus for buttressing a prosthetic cup for an acetabulum within the pelvis of a patient. An embodiment of a buttress plate 10 in accordance with the present invention is illustrated in FIG. 1. In operation, the buttress plate 10 is adapted to maintain a typical acetabular cup 20 within the acetabulum 32 of a pelvic girdle 30 to allow the cup to articulate with a prosthetic femoral head (not shown).

Figure 2:
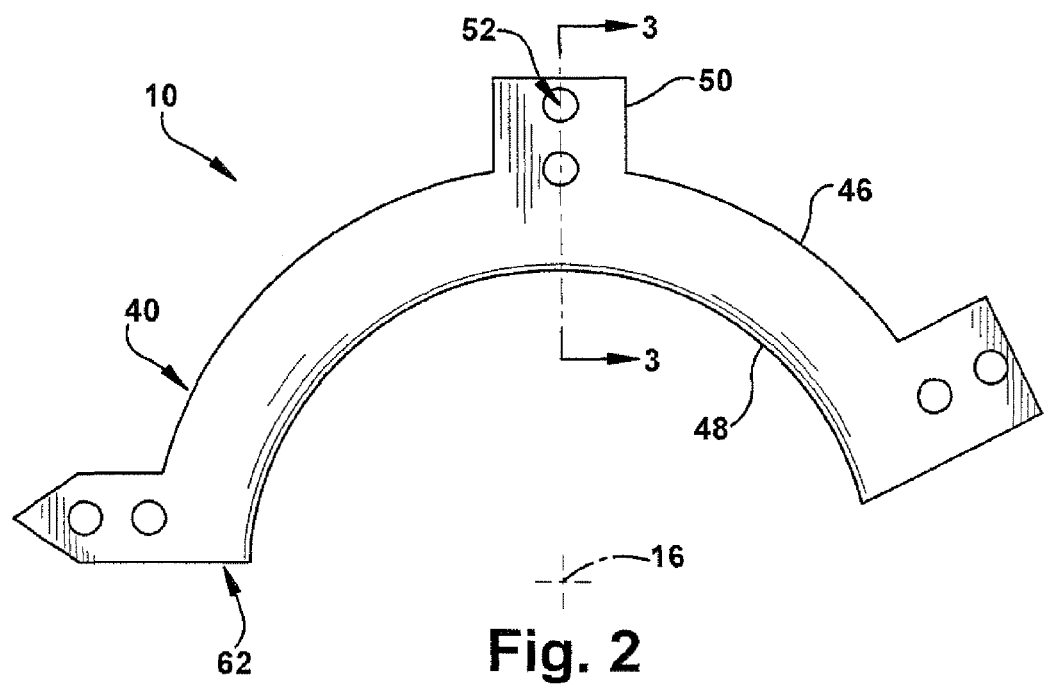
FIG. 2 is a top view of the plate of FIG. 1.
Figure 3:
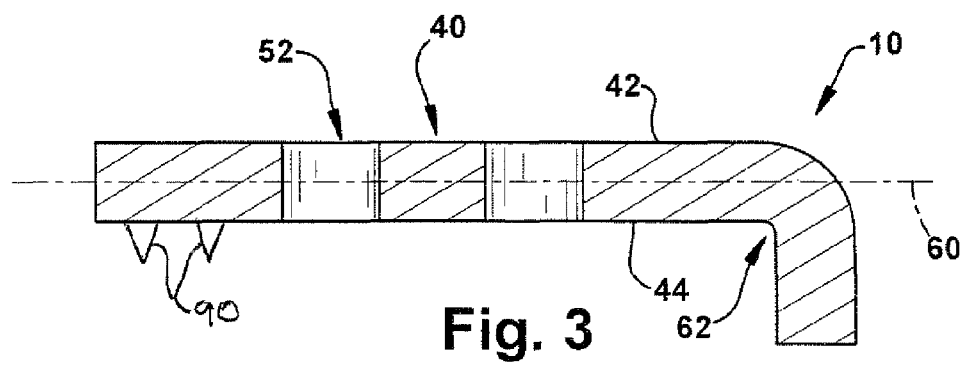
FIG. 3 is a sectional view of the plate of FIG. 2 taken along line 3-3.

The buttress plate 10 has an arcuate construction extending generally about an axis 16 and may, for example, be pre-contoured to the shape of the pelvis 34 of the patient. In particular, the buttress plate 10 may be pre-contoured to the posterior column of the acetabulum. The plate 10 includes a base 40 having a top surface 42 longitudinally spaced from a bottom surface 44. A first side portion 46 (or end) is laterally spaced from a second side portion 48 (or end) (FIGS. 2-3). The first side portion 46 and second side portion 48 extend generally parallel to one another or may have an oblique relation to one another. As shown in FIG. 2, the first side portion 46 and the second side portion 48 have a concentric relation to one another, with the first side portion being disposed radially outward of, and being laterally spaced from, the second side portion relative to the axis 16. Stated differently, the first and second side portions 46 and 48 are depicted in FIG. 2 as being curved and having coincident centers. The second side portion 48 in this concentric relationship is interposed laterally between the first side portion 46 and the axis 16.

The first side portion 46 of the base 40 includes at least one tab 50 which projects radially outward from the first side portion. Although three tabs 50 are illustrated in FIG. 2, it will be understood that the plate 10 may comprise more or fewer tabs, including a single tab. The tabs 50 are radially spaced from one another along the first side portion 46 in a uniform or non-uniform manner. Each tab 50 includes one or more passages 52 which extend longitudinally from the top surface 42 of the base 40 to the bottom surface 44 of the base. The passages 52 are sized to accommodate a fastener 80 to allow the plate 10 to be fixed to bone and in particular, to the pelvis 34.

The first side portion 46 of the base 40 and the tabs 50 extend generally along a plane 60 extending substantially parallel to the top surface 42 and the bottom surface 44 of the base. The second side portion 48 of the base 40 includes a lip 62 which extends at an angle relative to the plane 60. In particular, the lip 62 extends longitudinally downward and away from the top surface 42 of the base 40. Although FIG. 3 illustrates that the transition between the lip 62 and the remainder of the base 40 is arcuate, it will be understood that this transition may likewise be linear.

The bottom surface 44 of the base 40 may include means for engaging bone 90. The means 90 may include ribs, projections, or barbs, or may otherwise be textured or adapted to increase the ability of the bottom surface 44 of the base 40 to engage bone. Furthermore, the plate 10 may be mechanically, chemically, and/or biologically treated to promote bone growth once the plate has been installed within the patient.

The plate 10 is constructed of any biocompatible material capable of providing a secure fixation site at the pelvic girdle 30. The plate 10 can be made of metal, polymers, or combinations thereof. The plate 10 should be strong enough to maintain engagement with the pelvis 30 while the femoral head is articulating within the acetabular cup 20.

Figure 4:
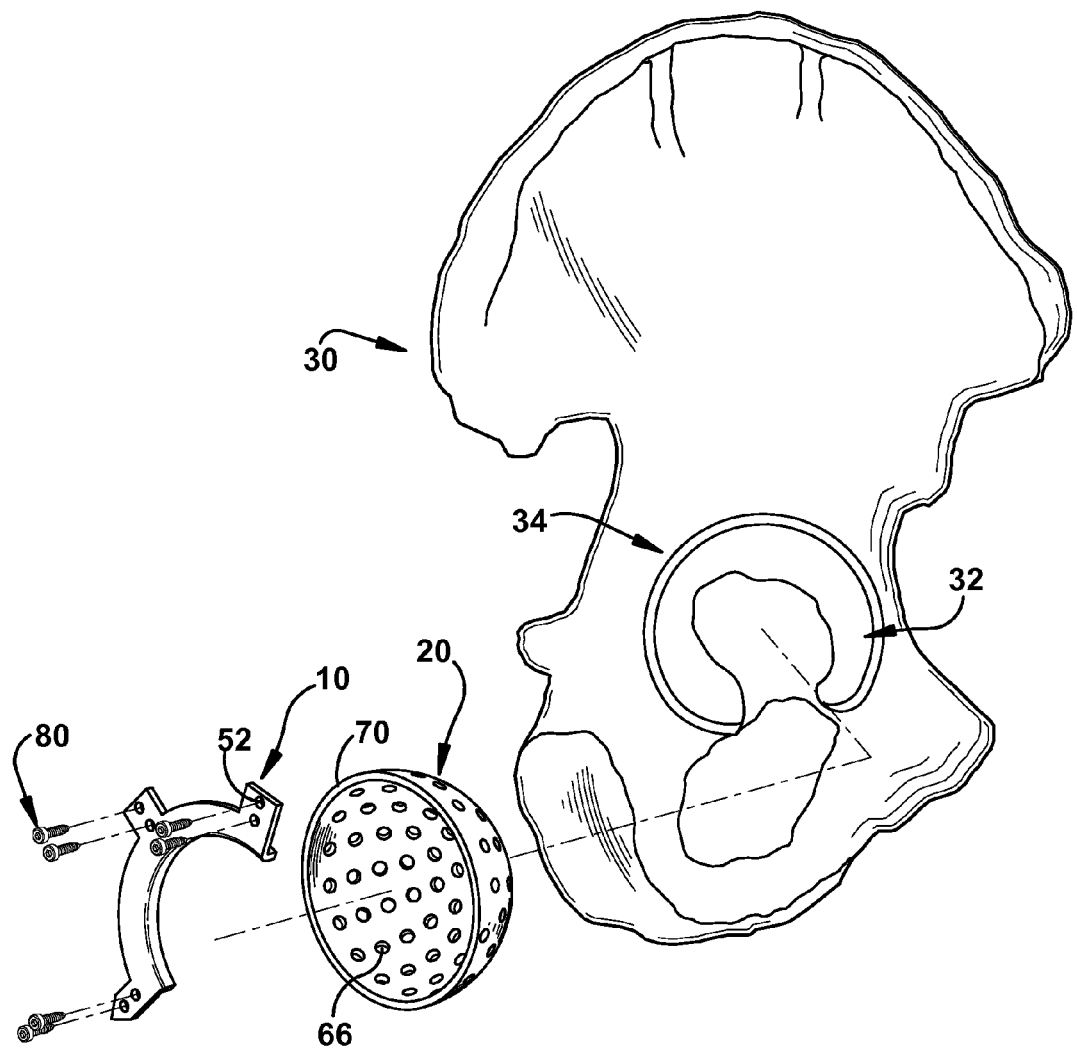
FIG. 4 is an exploded assembly view of the plate securing a support cup to the pelvis.

As shown in FIG. 4, the plate 10 is used as a buttress to ensure that the acetabular cup 20 remains in place within the pelvic girdle 30. Acetabular cups 20 are well known in the art. Typically, the cup 20 is pre-contoured to the shape of the native acetabulum 32 such that the cup can closely mimic the functionality of the acetabulum. The cup 20 has a generally cup-shaped construction and may include a plurality of holes 66 for facilitating the fastening of the cup to the acetabulum 32 via fasteners, screws, bone cement, etc.

Figure 5A:
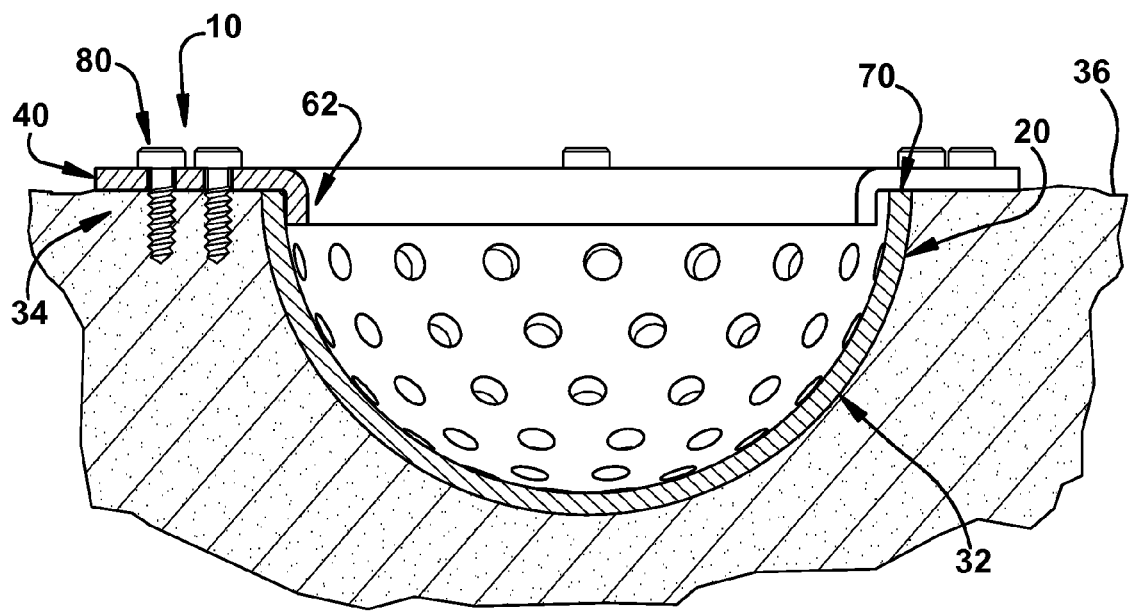
FIG. 5A is a sectional view of the plate retaining the cup within the acetabulum.

In operation, the cup 20 is placed within the acetabulum 32 such that a rim 70 of the cup is recessed from a lateral surface 36 of the pelvis 30 which helps define the acetabulum 32. As shown in FIG. 5A, the plate 10 is then positioned on the pelvis 34 such that the first side portion 46 of the base 40 overlies the lateral surface 36 and the lip 62 on the second side portion 48 of the base extends over the rim 70 of the acetabular cup 20 and into the acetabulum 32. In this configuration, the lip 62 overlies and engages a portion of the acetabular cup 20 below the rim 70, thereby placing a portion of the cup between the lip and the native acetabulum 32. Stated differently, the top surface 42 may be substantially located in a first plane, and at least a portion of the acetabular cup 20 is then interposed laterally between the lip 62 and the acetabulum 32 as these structures are laterally concentrically arranged (with respect to the axis 16) within a cross-section taken in a second plane parallel to, and longitudinally spaced from, the first plane.

A fastener or screw 80 is inserted into each passage 52 on the tabs 50 of the base 40. The fastener 80 includes a biocompatible screw or other structure suitable for penetration into bone. Each fastener 80 is screwed into the lateral surface 36 of the pelvis 34 until the head of the fastener applies a compressive force to the top surface 42 of the base 40 of the plate 10 to thereby pin the plate against the lateral surface (FIG. 5A). When the plate 10 becomes fixed to the pelvis 34, the lip 62 becomes fixed in an engaging fashion with the portion of the acetabular cup 20 below the rim 70, thereby preventing the cup from moving within the acetabulum 32. This configuration can ensure that the articulation between the acetabular cup 20 and the femoral head remains stable and more closely resembles natural articulation. Due to this stable connection and/or the use of bone growth-promoting materials, this construction may contribute to proper healing at the implant site.

Figure 5B:
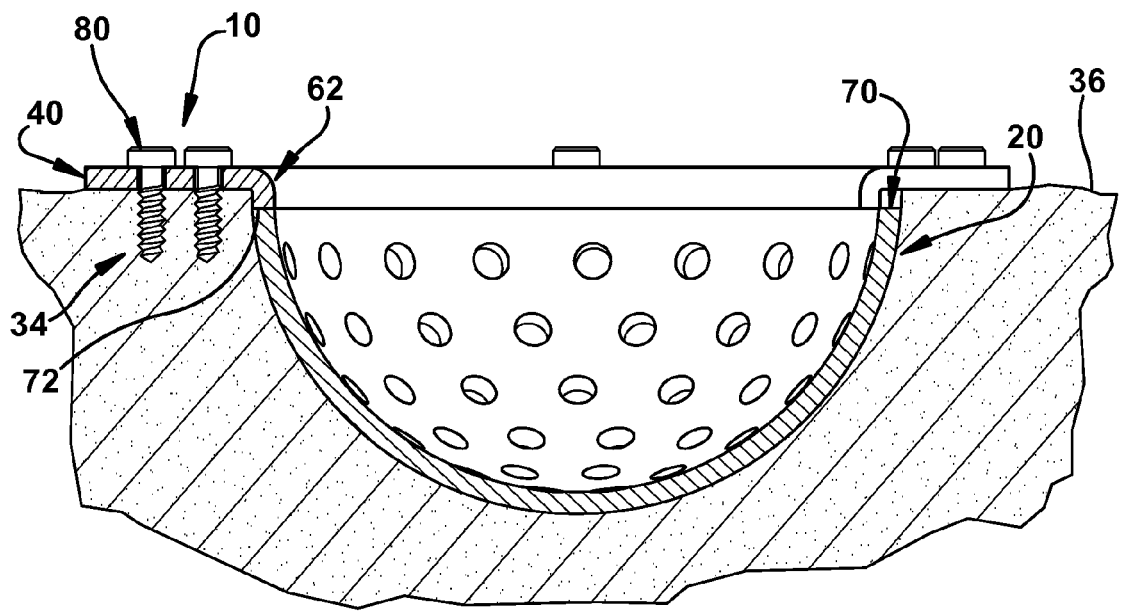
FIG. 5B is a sectional view of the plate retaining the cup within the acetabulum in accordance with another embodiment of the present invention.

Alternatively, the lip 62 on the base 40 of the plate 10 may be configured such that when the plate is placed across the pelvis 34, the lip overlies and engages a top surface 72 of the rim 70 of the acetabular cup 20 (FIG. 5B). In this construction, each fastener 80 is screwed into the lateral surface 36 of the pelvis 34 until the head of the fastener 80 applies a compressive force to the top surface 42 of the base 40 of the plate 10 to thereby pin the plate against the lateral surface. When the plate 10 becomes fixed to the pelvis 34, the lip 62 applies a compressive force to the top surface 72 of the rim 70 of the cup 20, thereby pinning the cup against the acetabulum 32 and preventing the cup from moving within the acetabulum.

Figure 6:
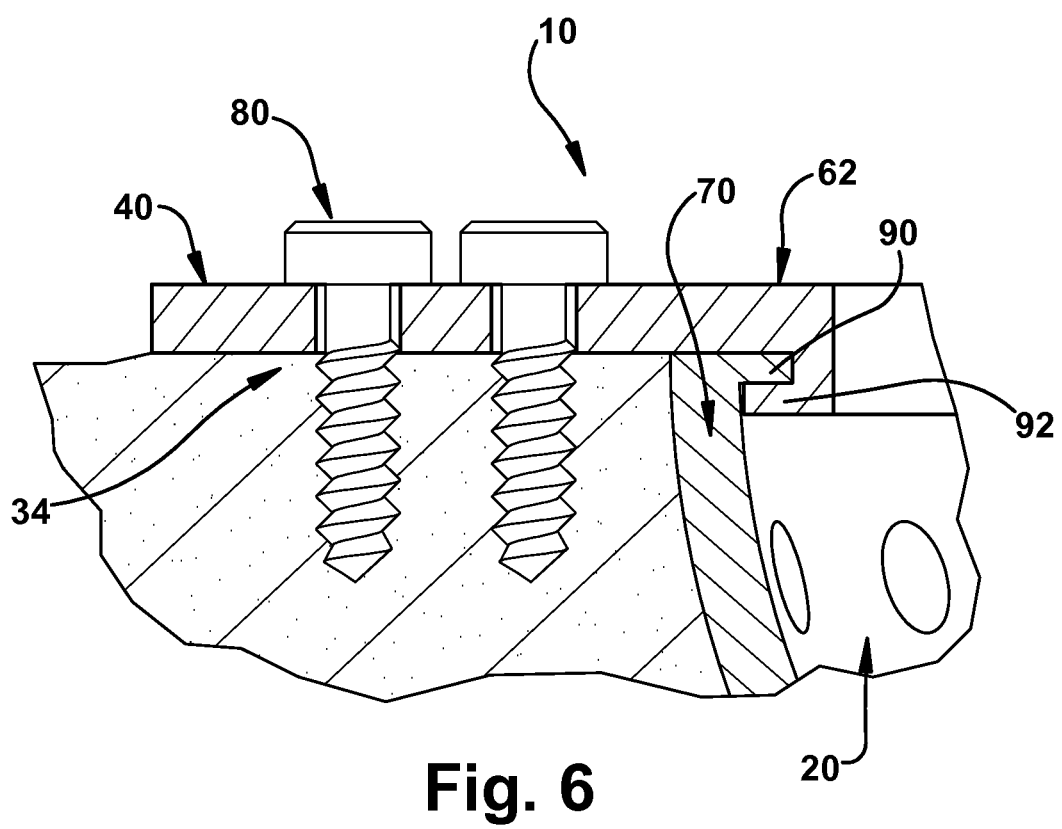
FIG. 6 is an enlarged view of the plate in accordance with another embodiment of the present invention.

In accordance with another aspect of the present invention, the lip 62 of the base 40 of the plate 10 and the rim 70 of the cup 20 may be configured with additional structure to mate with one another. The mating connection between the plate 10 and the cup 20 provides a more rigid engagement between the cup 20 and the acetabulum 32. In particular, the rim 70 of the cup 20 may include one or more projections 90 which engage one or more projection 92 on the lip 62 of the plate 10 (FIG. 6). The projection 92 on the lip 62 may be configured to snap over the projection 90 on the rim 70 as the base 40 is secured onto the lateral surface 36 of the pelvis 34. Those in the art will understand, however, that the plate 10 and the cup 20 can include other or additional mating features that increase the likelihood that the cup remains rigidly secured in the acetabulum 32.

From the above description of the invention, those skilled in the art will perceive improvements, changes and modifications. Such improvements, changes and modifications within the skill of the art are intended to be covered by the appended claims.

The invention claimed is:

1. A buttress plate for retaining an acetabular cup implanted in an acetabulum, the acetabular cup having an acetabular cup rim with a circumference, the buttress plate comprising:

an arcuate base extending generally about a longitudinally-oriented axis and having a first side portion laterally spaced from a second side portion, the first side portion extending along a plane and including at least one tab extending laterally outward from the first side portion, the base extending arcuately along less than a full circumference of the acetabular cup rim, each tab including at least one passage for receiving a fastener to secure the base to the acetabulum, the second side portion being laterally interposed between the first side portion and the axis, the second side portion including an arcuate lip extending transverse to the plane for securing the acetabular cup within the acetabulum, the base further including means for engaging bone and the plate further including a bone growth-promoting material for promoting bone growth.

2. The buttress plate of claim 1, wherein the base is pre-contoured to a pelvis.

3. The buttress plate of claim 1, wherein at least a portion of the plate simultaneously overlies and contacts at least a portion of circumferences of both a rim of the acetabulum and a rim of the acetabular cup, the acetabular cup extending concentrically with the rim of the acetabulum, to help secure the acetabular cup within the acetabulum.

4. The buttress plate of claim 1, wherein at least a portion of the acetabular cup is interposed between the lip and the acetabulum.

5. The buttress plate of claim 1, wherein the plane is a first plane, and at least a portion of the acetabular cup is interposed laterally between the lip and the acetabulum within a cross-section taken in a second plane parallel to, and longitudinally spaced from, the first plane.

6. The buttress plate of claim 1, wherein the arcuate base extends arcuately along less than half of the circumference of the acetabular cup rim.

7. A buttress plate for retaining an acetabular cup implanted in an acetabulum, the buttress plate comprising:

a base having a first side portion and a second side portion separated by a top surface, the first side portion extending along a plane and including at least one passage for receiving a fastener to secure the base to the acetabulum, the top surface being substantially located in the plane, the first and second side portions having a concentric relationship to each other provided by the first and second side portions being curved with a substantially common center, and the second side portion including a lip extending transverse to the plane and downward and away from the top surface, for securing the acetabular cup within the acetabulum, wherein the plane is a first plane, and at least a portion of the acetabular cup is interposed laterally between the lip and the acetabulum within a cross-section taken in a second plane parallel to, and longitudinally spaced from, the first plane.

8. The buttress plate of claim 7, wherein at least a portion of the plate simultaneously overlies and contacts at least a portion of circumferences of both a rim of the acetabulum and a rim of the acetabular cup, the acetabular cup extending concentrically with the rim of the acetabulum, to help secure the acetabular cup within the acetabulum.

\* \* \* \* \*